(12) United States Patent
Kesinger et al.

(10) Patent No.: US 10,456,059 B2
(45) Date of Patent: Oct. 29, 2019

(54) NEUOROLOGICAL CONDITION DETECTION UNIT AND METHOD OF USING THE SAME

(71) Applicant: Forest Devices, Inc., Pittsburgh, PA (US)

(72) Inventors: Matthew Kesinger, Pittsburgh, PA (US); Dan Willis, Pittsburgh, PA (US)

(73) Assignee: Forest Devices, Inc., Pittsburgh, PA (US)

( * ) Notice: Subject to any disclaimer, the term of this patent is extended or adjusted under 35 U.S.C. 154(b) by 347 days.

(21) Appl. No.: 15/083,366

(22) Filed: Mar. 29, 2016

(65) Prior Publication Data

US 2016/0287127 A1 Oct. 6, 2016

Related U.S. Application Data

(60) Provisional application No. 62/143,364, filed on Apr. 6, 2015.

(51) Int. Cl.
*A61B 5/0484* (2006.01)
*A61B 5/00* (2006.01)
*A61B 5/04* (2006.01)

(52) U.S. Cl.
CPC .......... *A61B 5/0484* (2013.01); *A61B 5/4064* (2013.01); *A61B 5/6806* (2013.01);
(Continued)

(58) Field of Classification Search
CPC ... A61B 5/0024; A61B 5/0484; A61B 5/0006; A61B 5/0026; A61B 5/0028; A61B 5/4064; A61B 5/04018
(Continued)

(56) References Cited

U.S. PATENT DOCUMENTS 1,046,148 A 12/1912 Butler
3,340,867 A 9/1967 Kubicek et al.
(Continued)

FOREIGN PATENT DOCUMENTS

JP 2000126145 A 5/2000
KR 20100042875 A * 4/2010
(Continued)

OTHER PUBLICATIONS

Reschke, M. F., Anderson, D. J., & Homick, J. L. (1984). Vestibulospinal reflexes as a function of microgravity. Science, 225, p. 212(3). Retrieved from https://dialog.proquest.com/professional/docview/766802767?accountid=142257.*
(Continued)

*Primary Examiner* — Daniel L Cerioni
*Assistant Examiner* — Raymond P Dulman
(74) *Attorney, Agent, or Firm* — Buchanan Ingersoll & Rooney PC

(57) ABSTRACT

A neurological condition detection unit can include a computer device that is connected to at least two leads that are connectable to a patient for evoking a response from that patient via an electrical current passed through the leads (e.g. a shock) and at plurality of sensors connected to the computer device to sense how the left side and right side of the patient's brain reacts to the evoked event (e.g. the shock). The stroke detection device and/or neurological condition detection unit can be configured to output a warning when one side of the patient's brain is determined to react differently than the opposite side of the patient's brain by at least a pre-selected threshold value. The warning can include an identification of a nearby care facility that may be best suited for providing care to a patient determined to have a neurological condition (e.g. a stroke).

19 Claims, 7 Drawing Sheets

(52) U.S. Cl.
CPC .......... *A61B 5/0006* (2013.01); *A61B 5/0024* (2013.01); *A61B 5/04017* (2013.01); *A61B 5/04018* (2013.01); *A61B 5/6893* (2013.01); *A61B 2560/0475* (2013.01)

(58) Field of Classification Search
USPC ........................................................ 600/382
See application file for complete search history.

(56) References Cited

U.S. PATENT DOCUMENTS

| | | | |
|---|---|---|---|
| 3,696,808 A * | 10/1972 | Roy .................... | A61B 5/0484 600/544 |
| 3,774,594 A | 11/1973 | Huszar | |
| 3,960,141 A | 6/1976 | Bolduc | |
| 4,421,122 A | 12/1983 | Duffy | |
| 4,836,214 A | 6/1989 | Sramek | |
| 5,143,081 A * | 9/1992 | Young .................... | A61B 5/0484 600/554 |
| 5,331,966 A * | 7/1994 | Bennett .............. | A61N 1/36185 128/903 |
| 6,115,623 A | 9/2000 | McFee | |
| 6,233,472 B1 | 5/2001 | Bennett et al. | |
| 6,516,214 B1 | 2/2003 | Boas | |
| 6,625,485 B2 | 9/2003 | Levendowski et al. | |
| 6,804,661 B2 | 10/2004 | Cook | |
| 6,826,426 B2 | 11/2004 | Lange et al. | |
| 6,847,836 B1 | 1/2005 | Sujdak | |
| 6,947,790 B2 | 9/2005 | Gevins et al. | |
| 7,062,300 B1 * | 6/2006 | Kim .................... | B60R 11/0241 379/454 |
| 7,202,089 B2 | 4/2007 | Kleinfeld | |
| 7,257,438 B2 | 8/2007 | Kinast | |
| 7,558,622 B2 | 7/2009 | Tran | |
| 7,774,052 B2 | 8/2010 | Burton et al. | |
| 8,364,254 B2 | 1/2013 | Jacquin et al. | |
| 8,374,414 B2 | 2/2013 | Tang et al. | |
| 8,486,652 B2 | 7/2013 | Larue et al. | |
| 8,989,836 B2 | 3/2015 | Machon et al. | |
| 9,271,651 B2 | 3/2016 | Avinash et al. | |
| 9,282,930 B2 | 3/2016 | Machon et al. | |
| 2002/0111744 A1 * | 8/2002 | Buegner ................ | A61B 5/16 702/19 |
| 2003/0109799 A1 | 6/2003 | Brown | |
| 2004/0204837 A1 * | 10/2004 | Singleton .............. | G01C 21/20 701/410 |
| 2004/0249422 A1 | 12/2004 | Gliner et al. | |
| 2004/0267153 A1 * | 12/2004 | Bergethon ........... | A61B 5/0484 600/554 |
| 2005/0216071 A1 | 9/2005 | Devlin et al. | |
| 2007/0100278 A1 | 5/2007 | Frei et al. | |
| 2007/0244407 A1 * | 10/2007 | Osorio ................ | A61B 5/4094 600/544 |
| 2008/0146973 A1 * | 6/2008 | Lund .................... | A61H 31/00 601/40 |
| 2008/0208074 A1 | 8/2008 | Snyder et al. | |
| 2009/0211538 A1 * | 8/2009 | Corke .................. | A01K 29/005 119/720 |
| 2011/0190595 A1 * | 8/2011 | Bennett .............. | A61B 1/00016 600/301 |
| 2011/0218405 A1 | 9/2011 | Avinash et al. | |
| 2011/0245707 A1 | 10/2011 | Castle et al. | |
| 2011/0257510 A1 | 10/2011 | Weiss | |
| 2012/0059593 A1 * | 3/2012 | Konings ................ | A61B 5/029 702/19 |
| 2012/0143020 A1 | 6/2012 | Bordoley et al. | |
| 2012/0172747 A1 * | 7/2012 | Fukuda ................ | A61B 5/0537 600/547 |
| 2012/0182539 A1 * | 7/2012 | Grokop ................ | G01B 11/026 356/4.01 |
| 2012/0330109 A1 | 12/2012 | Tran | |
| 2013/0267818 A1 * | 10/2013 | David .................. | A61B 5/0006 600/382 |
| 2014/0121557 A1 * | 5/2014 | Gannon ................ | A61B 5/002 600/549 |
| 2014/0142410 A1 | 5/2014 | Erb et al. | |
| 2014/0249760 A1 * | 9/2014 | Proud .................... | A61B 5/443 702/19 |
| 2014/0257073 A1 | 9/2014 | Machon et al. | |
| 2014/0378779 A1 * | 12/2014 | Freeman .............. | A61B 5/0051 600/301 |
| 2015/0174418 A1 * | 6/2015 | Tyler .................... | A61B 5/055 601/2 |
| 2015/0282760 A1 | 10/2015 | Badower et al. | |
| 2016/0270679 A1 * | 9/2016 | Mahon ................ | A61B 5/04001 |

FOREIGN PATENT DOCUMENTS

| | | |
|---|---|---|
| WO | 2004093642 A2 | 11/2004 |
| WO | 20140184904 A1 | 11/2014 |

OTHER PUBLICATIONS

Ugawa, et al., Modulation of Motor Cortical Excitability by Electrical Stimulation Over the Cerebellum in Man, 1991, Journal of Physiology, 441, p. 57-72.*
Kanda, et al., Primary somatosensory cortex is actively involved in pain processing in human, 2000, Brain Research, 853, p. 282-289.*
KR 20100042875 Specification English Translation (Year: 2010).*
International Search Report for PCT/US2016/024905 dated Jul. 14, 2016.
Written Opinion of the International Searching Authority for PCT/US2016/024905 dated Jul. 14, 2016.
Journal of Clinical Monitoring and Computing (2005) 19: 77-168, "Cerebral Monitoring in The Operating Room and the Intensive Care Unit—An Introductory for the Clinician and a Guide for the Novice Wanting to Open a Window to the Brain" by Enno Freye, MD, PhD.

* cited by examiner

NEUOROLOGICAL CONDITION DETECTION UNIT AND METHOD OF USING THE SAME

CROSS-REFERENCE TO RELATED APPLICATIONS

This patent application claims priority to U.S. Provisional Patent Application No. 62/143,364, which was filed on Apr. 6, 2015.

FIELD OF INVENTION

The present invention relates to devices configured to detect a stroke and/or a condition indicative of at least one neurological disease and methods of using such devices.

BACKGROUND OF THE INVENTION

It can often be difficult for emergency responders or minimally trained medical personnel to detect a patient having a stroke or detect a patient who is about to have a stroke. For instance, medics, such as paramedics, emergency service ("EMS") personnel, or emergency medical technician ("EMT") personnel are often unable to readily detect whether a patient has experienced a stroke. Often, medics will take a patient to the nearest hospital, which may not be able to provide care to stroke patients. For instance, only about 1 in 7 hospitals are currently configured as stroke centers.

Currently, a computerized tomography (CT) scan is often the only objective method regularly used to detect whether a patient has experienced a stroke. But, a CT scanner can be difficult to incorporate into tools an emergency responder or other patient care provider may regularly use, such as an ambulatory vehicle, urgent care center, or general practitioner doctor's office. Therefore, pre-hospital providers often only have subjective clinical exams to rely upon for the detection of a stroke in a patient, which are in large part dependent on the skill and experience of a particular care provider.

SUMMARY OF THE INVENTION

A neurological condition detection unit, a stroke detection device, methods of using such devices, and methods of detecting a stroke for routing of an ambulance (e.g. ambulatory truck, van, boat, airplane, helicopter or other vehicle transporting a patient to a hospital) are provided herein. Embodiments of the stroke detection device and/or neurological condition detection unit can include a computer device that is connected to at least two leads that are connectable to a patient for evoking a response from that patient via an electrical current passed through the leads (e.g. a shock) and a plurality of sensors connected to the computer device to sense how the left side and right side of the patient's brain reacts to the evoked event (e.g. the shock). The stroke detection device and/or neurological condition detection unit can be configured to output a warning when a comparison of two or more areas of the patient's brain reacts to the evoked event (e.g. the shock) shows that one area has responded substantially differently than another area to the evoked event (e.g. the shock). For instance, a stroke may be detected when one side of the patient's brain is determined to react differently than the opposite side of the patient's brain by at least a pre-selected threshold value. The warning that is output may be communicated by the stroke detection device so that a warning is displayed via an output device (e.g. a display and/or a speaker, etc.) to inform an emergency responder, such as a medic, that the patient has experienced a stroke or may have experienced a stroke so that the patient can be transported to a hospital that is capable of providing effective treatment for the patient. Embodiments of the neurological condition detection unit can be configured to provide physiological data to for an out-of-hospital patient so that a pre-hospital care provider (e.g. medic, emergency responder, other minimally trained medical assistant, etc.) can utilize the unit to obtain objective physiological data that may facilitate detection of a stroke or other neurological condition without requiring substantial reliance on the care giver's skill and experience.

In some embodiments, the neurological condition detection unit can be configured so that electrodes and sensors need not be placed in the hair of a patient (e.g. after shaving or otherwise removing hair on the head of a patient or after removal of hair on the arms or legs of a patient, etc.). Such embodiments can allow for easy electrode and sensor placement that allows for relatively quick placement for detecting a neurological condition via the unit.

In some embodiments, a method for detecting a neurological condition includes the steps of attaching evoked electrodes on opposite sides of a body, positioning sensors on the opposite sides of the body, communicatively connecting the evoked electrodes and the sensors to a computer device having non-transitory memory connected to a processor, using the computer device to shock the body via the evoked electrodes for a pre-selected number of shocks within a pre-selected time period, the computer device generating at least one of wave forms and curves that identify morphological features for responses from the pre-selected number of shocks the opposite sides of the body are measured to have, the computer device comparing the morphological features to determine a difference between a morphological feature for a left side of the body and a morphological feature for a right side of the body that is at or exceeds a pre-selected threshold, and the computer device generating a notification to identify a detection of a neurological condition in response to a result of the comparing of the morphological features indicating that the difference between the morphological feature for the left side of the body and the morphological feature for the right side of the body is at or exceeds the pre-selected threshold.

In some embodiments the at least one of the wave forms and the curves are generated from measurement data the computer device receives from the sensors. This data may also be generated after filtration of measurement data and processing such data to remove noise or other components of the measurement data that may be considered inaccurate data or data having no little significance to the evaluation of the patient's condition. For instance, some embodiments of the method can also include filtering measurement data received from the sensors for generating the at least one of the wave forms and the curves. The method can also include other steps. For instance, the method can include the computer device receiving the measurement data from the sensors and storing the measurement data in the memory. The storage of the data may occur before the data is filtered and/or otherwise processed.

In some embodiments, the morphological features can be amplitudes and the responses from the pre-selected number of shocks the opposite sides of the body can be electrical responses a central nervous system of the body has to the pre-selected number of shocks.

The notification can includes indicia identifying a location of a hospital determined to be most capable of providing care for the neurological condition. The computer device can also search at least one data store to identify a hospital based on the detected neurological condition that may be best qualified to treat that condition within a pre-selected distance of the computer device and/or patient and communicate data to an output device for identifying directions for routing an ambulatory vehicle to the hospital during implementation of the method. Additionally, the computer device can communicate data to a communication system of the hospital relating to the detection of the neurological condition.

In some embodiments, the evoked electrodes can be on pads that are adhesively attached to the body for removable attachment to the body and the sensors can be on at least one pad that is adhesively attached to the body. In some embodiments, the pads having the evoked electrodes can also have at least one of the sensors. These pads may have coverings that cover the adhesive portions of the pads. Each of the coverings can have indicia identifying a location on which the pad of that covering is to be positioned on the body. Embodiments of the method can also include the step of removing the coverings that cover adhesive portions of the pads prior to those pads being positioned on a patient. The evoked electrodes can be positioned adjacent left and right wrists of the body and the sensors can be positioned on a head of the body or on a neck of the body in some embodiments of the method. The indicia of the coverings may identify these locations for these embodiments.

In other embodiments, the evoked electrodes are on gloves or in gloves and the attaching of the evoked electrodes on opposite sides of the body includes inserting hands of the body into the gloves. The gloves can be configured to have one or more visual verification mechanisms that can be viewed by a medic or other care provided to verify that the gloves are not twisted or otherwise improperly positioned on the patient.

In some embodiments of a neurological condition detection unit, the unit can include non-transitory memory, a processor connected to the memory, a plurality of evoked electrodes connectable to the neurological condition detection unit such that a pre-selected number of shocks within a pre-selected time period is transmittable into a body of a patient via the evoked electrodes, and a plurality of sensors communicatively connectable to the memory such that measurement data relating to responses opposite sides of the body of the patient have to the shocks is storable in the memory. The neurological condition detection unit can be configured to utilize the measurement data to generate at least one of wave forms and curves that identify amplitudes for responses from the shocks the opposite sides of the body are measured to have, compare the amplitudes to determine a difference between an amplitude for a left side of the body and an amplitude for a right side of the body that is at or exceeds a pre-selected threshold; and generate a notification to identify a detection of a neurological condition in response to a result of the comparing of the amplitudes indicating that the difference between the amplitude for the left side of the body and the amplitude for the right side of the body is at or exceeds the pre-selected threshold.

In some embodiments, the neurological condition detection unit is positioned in an ambulatory vehicle so that the device is portable or mobile. The neurological condition detection unit can also include at least one wireless transceiver unit configured to communicatively connect the processor and the memory to the sensors and/or the evoked electrodes.

Embodiments of the neurological condition detection unit can also include a power source connected to the evoked electrodes such that electricity is transmittable into the body via the evoked electrodes. The power source may be a battery within a housing of a computer device or may be a battery of a vehicle in which the neurological condition detection unit is positionable or may be an engine of a vehicle in which the neurological condition detection unit is positionable. In some embodiments, the neurological condition detection unit may be portable and be positionable outside of a vehicle but still be coupled to the vehicle engine and/or battery as its power source for providing power to evoked electrodes.

In some embodiments, the sensors are on at least one pad that is configured to adhesively attach to the body and the evoked electrodes are on pads that are configured to adhesively attach to the opposite sides of the body. The pads can each have a covering that removably covers adhesive of the pad that is configured to adhesively attach the pad to the body. The covering can have indicia identifying a location on the body to which the pad is to be attached.

It is contemplated that some embodiments of neurological condition detection unit can include non-transitory memory, a processor connected to the memory, one or more visual stimulation mechanisms connectable to the neurological condition detection unit such that a pre-selected number of visual stimulation within a pre-selected time period is transmittable into one or more eyes of a patient via the visual stimulation mechanisms, and a plurality of sensors communicatively connectable to the memory such that measurement data relating to responses opposite sides of the body of the patient have to the visual stimuli is storable in the memory. The neurological condition detection unit can be configured to utilize the measurement data to generate at least one of wave forms and curves that identify amplitudes for responses from the visual stimuli the opposite sides of the body are measured to have, compare the amplitudes to determine a difference between an amplitude for a left side of the body and an amplitude for a right side of the body that is at or exceeds a pre-selected threshold, and generate a notification to identify a detection of a neurological condition in response to a result of the comparing of the amplitudes indicating that the difference between the amplitude for the left side of the body and the amplitude for the right side of the body is at or exceeds the pre-selected threshold.

It is also contemplated that embodiments of the method for detecting a neurological condition can include positioning at least one visual stimulation device to on a head of a patient, positioning sensors on the opposite sides of the body of the patient, communicatively connecting the at least one visual stimulation device and the sensors to a computer device having non-transitory memory connected to a processor, using the computer device to actuate visual stimuli to the eyes of the patient via the one or more visual stimulation devices for a pre-selected number of visual stimuli within a pre-selected time period, the computer device generating at least one of wave forms and curves that identify morphological features for responses from the pre-selected number of visual stimuli the opposite sides of the body are measured to have, the computer device comparing the morphological features to determine a difference between a morphological feature for a left side of the body and a morphological feature for a right side of the body that is at or exceeds a pre-selected threshold, and the computer device generating a notification to identify a detection of a neurological condition in response to a result of the comparing of the morphological features indicating that the difference between the morphological feature for the left side of the body and the morphological feature for the right side of the body is at or exceeds the pre-selected threshold.

In some embodiments of the method or neurological condition detection unit, the computer device or the neurological condition detection unit can also be configured to utilize multiple evoked electrodes for providing evoked potential via electrical stimulation to a patient in addition to use of the visual stimulation via one or more visual stimulation devices and/or visual stimulation mechanisms.

In some embodiments, the visual stimulation mechanisms and/or the visual stimulation devices may include one or more light emitting devices such as light emitting diodes or one or more pen lights. These mechanisms may have a wireless communicative connection and/or a wired connection to a computer device and/or a component of the neurological condition detection unit.

Other details, objects, and advantages of the invention will become apparent as the following description of certain exemplary embodiments thereof and certain exemplary methods of practicing the same proceeds.

BRIEF DESCRIPTION OF THE DRAWINGS

Exemplary embodiments of a neurological condition detection unit are shown in the accompanying drawings and certain exemplary methods of practicing the same are also illustrated therein. It should be appreciated that like reference numbers used in the drawings may identify like components.

DETAILED DESCRIPTION OF EXEMPLARY EMBODIMENTS

Figure 1:
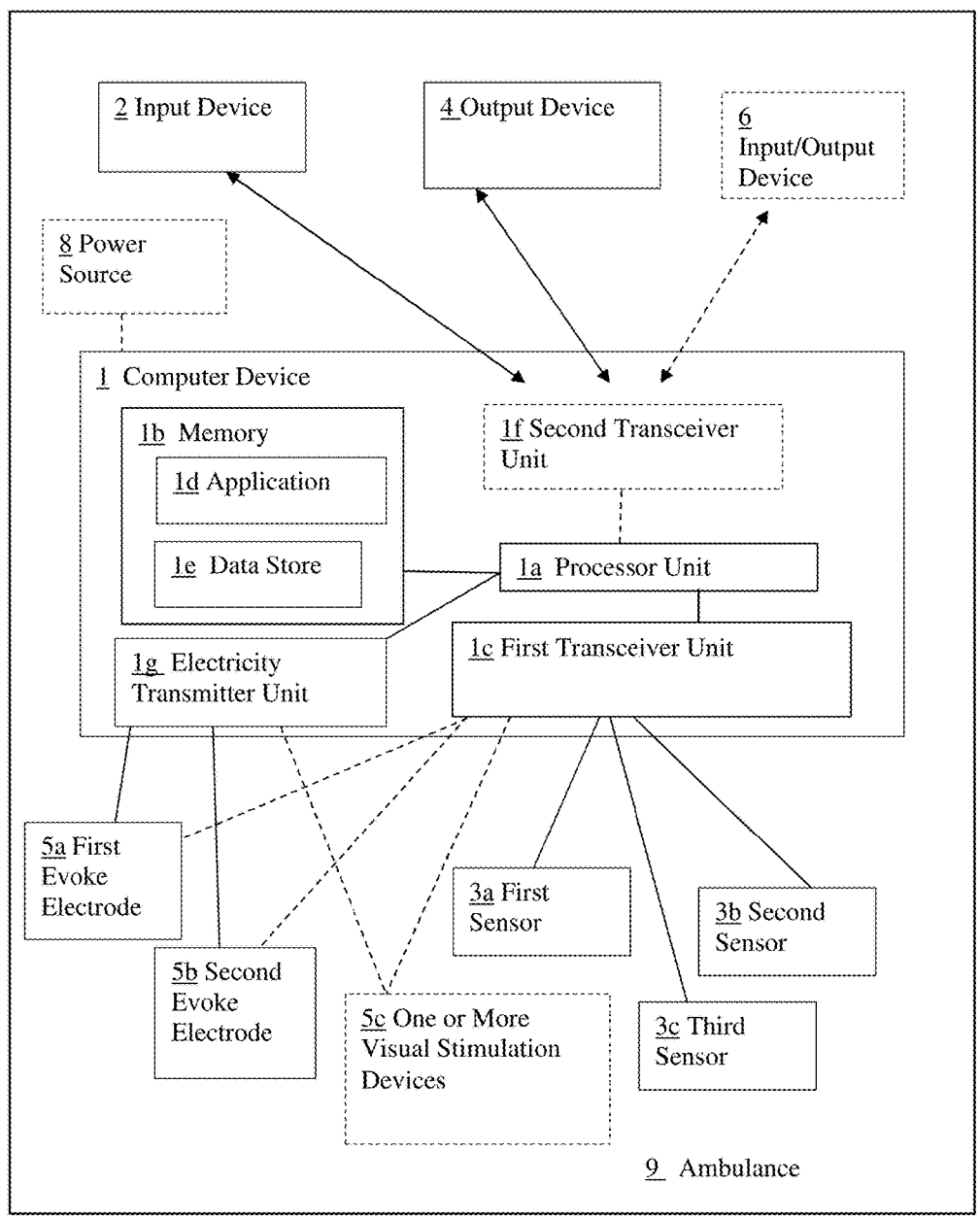
FIG. 1 is a block diagram of a first exemplary embodiment of a neurological condition detection unit.

Referring to FIGS. 1-5, embodiments of a neurological condition detection unit can be configured as a stroke detection device, or stroke detection apparatus. This device can include a computer device 1. The computer device 1 can be an electronic device that is electrically connected to an electrical circuit of an ambulance 9. For instance, a power source 8 of an ambulance 9 (e.g. an ambulatory vehicle such as a medical helicopter, ambulatory truck, ambulatory van, etc.) can be electrically connected to the computer device 1 to transmit electricity to the computer device 1 to power the computer device 1. In some embodiments, the power source 8 can be a battery of the ambulance or the internal combustion motor of the ambulance 9. In other embodiments, the power source may be a battery that is located in a housing of the computer device or is another type of electrical power source configured to provide electricity to the computer device 1 to power the operation of the computer device 1.

The computer device can include hardware. The hardware may include a processor unit 1a that is communicatively connected to non-transitory memory 1b and at least one first transceiver unit 1c. The non-transitory memory may be internal memory of the computer device, flash memory, a hard drive, or other type of tangible, non-transitory computer readable medium. The memory 1b can store at least one application 1d and at least one data store 1e. The application may be a computer program having code that is executed by the processor 1a so that the computer device 1 performs a method defined by the code. The code may include code that requires use of predefined functions, data stored in data stores 1e, or data to be received from other elements connected to the processor 1a when the processor is running the application to perform the method defined by the code. The data store 1e can be one or more databases or other type of data stored in the memory 1b. The processor unit 1a can be an electrical processor such as a central processing unit ("CPU"), at least one microprocessor, at least one core processor, interconnected processors that are connected in series or in parallel, or other type of processor electrical device. The first transceiver unit 1c can include at least one receiver and at least one transmitter. The first transceiver unit 1c can include an interface for permitting the processor unit 1a and/or memory 1b to receive data from and/or provide data to other devices, such as an input device 2, an output device 4, an input/output device 6, and/or a plurality of sensors (e.g. first sensor 3a, second sensor 3b, and third sensor 3c, etc.). The sensors may be configured to detect electrical potentials or other type of neural signals from a patient. In some embodiments, the sensors may be combined with infrared sensors to detect blood oxygen saturation or temperature as well.

The number of sensors that are used in embodiments of the device can include any number of different arrays of sensors. For instance, there may be more than two sensors, more than three sensors more than five sensors, or more than 10 sensors that are used. In some embodiments, the sensors may be included in one or more pads, one or more patches, a headband, one or more wearable straps, one or more wearable bands or in other wearable mechanisms that may be configured to facilitate attachment of the sensors to a patient at desired locations.

The first transceiver unit 1c can also be configured so that the processor 1a is communicatively connectable to other devices such as at least one hospital communication device 13 and/or a communication device hosting a location service 11. The processor unit 1a can also be connected to at least one second transceiver unit 1f and an electricity transmitter unit 1g.

Each input device can be a device configured to allow a user to provide input to a processor unit 1a. For instance, demographic information about a patient may be input by a provider using an input device (e.g. keyboard, mouse, touch screen, etc.) to identify the sex of a patient, the age or age range of the patient (e.g. 27 years old or 25-35 years old, or an age within 5 or 10 years of the patients actual age, etc.). Other information about the patient can also be provided as input to the device via an input device. The entered information can be stored in the memory of the device for use by the device when assessing the patient's responses to evoked potential, or "shocks" that may be provided to the patient via electrodes.

An input device can include a touch screen display, a stylus, a keyboard, a pointer device, a mouse, a keypad, one or more buttons, a microphone, or other type of input mechanism. Some of the input devices may be internal to a housing of the computer device 1 and be communicatively connected to the processor 1a via wiring or other communicative connection. Input devices 2 may also (or alternatively) be communicatively connected to the processor 1a via a short range radio connection (e.g. a Bluetooth connection or near field communication connection) or a wired connection (e.g. a Universal Serial Bus ("USB") connection).

Each output device may be a device configured to output data to a user. Examples of an output device 4 that may be connected to the processor 1a of the computer device 1 include a display unit, a liquid crystal display, a monitor, a printer, at least one speaker, or other type of output mechanism. Some of the output devices may be internal to a housing of the computer device 1 and be communicatively connected to the processor 1a via wiring or other communicative connection. Output devices 4 may also (or alternatively) be communicatively connected to the processor 1a via a short range radio connection (e.g. a Bluetooth connection) or a wired connection (e.g. a USB connection).

Input/output devices 6 that may be connected to the processor unit 1a can be configured to provide output to a user and can also be configured to provide input to the processor 1a. Examples of an input/output device can include a touch screen display device. Some of the input/output devices may be internal to a housing of the computer device 1 and be communicatively connected to the processor 1a via wiring or other communicative connection. Input/output devices 6 may also (or alternatively) be communicatively connected to the processor 1a via a short range radio connection (e.g. a Bluetooth connection) or a wired connection (e.g. a USB connection).

Each input device 2, output device 4 and/or input/output device 6 can be communicatively connected to the processor 1a and/or memory 1b via the first transceiver unit 1c. Alternatively, a second transceiver unit 1f can be configured to communicatively connect these elements to the processor unit 1a and/or memory 1b. For instance, in some embodiments, the first transceiver unit 1c can be configured to provide communication connections via a first type of connection mechanism (e.g. a wireless network connection, a local radio connection, a wired communicative connection, a wireless connection to a base station of a wide area network or cellular network, etc.) and the second transceiver unit 1f can be configured to provide a second type of communicative connection (e.g. a USB connection). In yet other embodiments, the computer device 1 can include multiple other types of transceiver units. In yet other embodiments, the first transceiver unit 1c can be configured to include multiple different types of transceivers for communicative connections of the computer device 1 to different devices via different types of connection protocols or methodologies.

The electricity transmitter 1g can be connected to multiple leads such as, for example, a first evoked electrode 5a and a second evoked electrode 5b. Each evoked electrode can be attached to a pad for attachment to or positioning on a patient and can be configured for the transmission of stimuli to an object. For instance, each evoked electrode may be configured to include an anode and a cathode and the electricity transmitter 1g can be connected to these evoked electrodes so that an electrical current can be transmitted to these electrodes for being transmitted to another object, such as a patient. Each evoked electrode can be included as a component of a wrist band, ankle band, behind the knee band, or other type of strap, patch or other type of wearable device configured for being placed in contact on a human patient. For instance, the first evoked electrode 5a may be connected to a first strap configured to be placed around a patient's left wrist, left ankle, left shoulder, left thorax, or behind the patient's left knee so that the first evoked electrode 5a is in contact with the patient's skin near a nerve on the left side of the patient's body the second evoked electrode 5b may be connected to a second strap that is configured to be placed around a patients right wrist, right ankle, behind the patient's right knee, on the patient's right shoulder, or right thorax so that the second evoked electrode 5b contacts the patient's skin near a nerve on the right side of the patient's body. The evoked electrodes may be positioned so that they are positioned on the median nerves of the patient on the left and right sides of the patient. The evoked electrodes may also (or alternatively), be positioned on the ulnar, tibial, peroneal (also known as the fibular), axiliary, musculocutaneous, brachial plexus, accessory nerves and/or other sensory nerves that communicate with the central nervous system (e.g. somatosensory cortex and/or other parts of the central nervous system).

In some embodiments, the positioning of the first and second evoked electrodes 5a, 5b can correspond to one another on opposite sides of a patient for being positioned on opposite sides of a patient's nerve or on corresponding sides of the same type of nerve of the patient. For instance, if the first evoked electrode 5a is positioned on a patient's left wrist, the second evoked electrode 5b may be placed on the patient's right wrist so that the positions of the first and second evoked electrodes correspond to one another on opposite sides of the patient. As another example, if the first evoked electrode 5a is positioned on a patient's right ankle, the second evoked electrode 5b may be placed on the patient's left ankle so that the positions of the first and second evoked electrodes correspond to one another on opposite sides of the patient.

The electricity transmitter can be configured to transmit electricity to each evoked electrode so that a current of 5 milliamps (mA), a current of no greater than 200 mA, or another current having a pre-selected value (e.g. 5 mA to 200 mA, 50 mA to 200 mA, 50 mA, 200 mA, or greater than 200 mA or less than 5 mA but greater than 0 mA, etc.) is passed into the patient having the first and second evoked electrodes 5a, 5b (as well as any other additional evoked electrodes)

contacting the patient's body so that a sensory evoked potential can be generated in the patient's body in response to the shock provided by the current. The current may be continuously transmitted by the electricity transmitter unit 1g for a pre-selected time range, such as, for example less than 1 second, less than 0.5 seconds, less than 0.33 seconds, less than 0.25 seconds, or for some other pre-selected time range. After that time range passed, the electricity may be stopped for at least a brief duration of time.

In some embodiments, one or more visual stimulation devices 5c can be connected to at least one of the electricity transmitter 1g and/or the first transceiver unit 1c and/or the second transceiver unit if such that the computer device can communicate with the one or more visual stimulation devices 5c and/or transmit electricity to visual stimulation mechanisms 53 of that device to provide power for providing a visual stimulus to a patient. Such a stimulation may be activation of lights in a patient's left eye, right eye, or both eyes. The visual stimulation may occur at the same time in both eyes and/or at different times for different eyes. Each visual stimulation mechanism 53 may include, for example, light emitting diodes or other type of light emitting devices. These light emitting devices may be positioned in glasses, goggles, a helmet having a visor, or other type of headgear that may be positioned on a patient's head to position the visual stimulation mechanism near the patient's eyes to provide the visual stimulus to the patient. The one or more visual stimulation devices 5c can be used as an alternative to evoked electrodes 5a and 5b or may be used in combination with those evoked electrodes to provide stimulus to a patient to measure how the patient's body reacts to that stimulus for purposes of evaluating at least one neurological condition of the patient.

In some embodiments, the device may be configured to take measurements via at least one of the sensors to measure the amount of power required to stimulate a patient at a specified current. The device can be configured to receive such measurement data from one or more of the sensors to determine skin impedance, placement orientation issues and/or sweat levels of the patient. In the event a placement orientation issue is detected, the device can be configured to cause a warning to be emitted to having the electrodes re-positioned to be correctly positioned by a user. The device can also be configured to calibrate other measurement data it receives from the sensors based on the skin impedance and/or sweat level measurement data.

In some embodiments, more than two evoked electrodes may be used. For example, there may be more than two evoked electrodes, more than four evoked electrodes, or more than six evoked electrodes. In yet other embodiments, only two evoked electrodes may be used.

A plurality of sensors can also be connected to the processor unit 1a. The sensors can include a first sensor 3a, a second sensor 3b, and a third sensor 3c. The sensors may also include additional sensors (e.g. a fourth sensor, a fifth sensor, a sixth sensor, etc.). In some embodiments, the sensors may be configured as electrodes or include electrodes such as electroencephalogram (EEG) electrodes and/or electrocardiogram (also referred to as "ECG" or "EKG") electrodes. In other embodiments, the sensors may include other types of electrodes that may be placed on a patient's head and/or neck to detect the response to the evoked potentials in the patient's brain and/or evoked potentials of a patient's head and neck. The first sensor 3a can be configured for being positioned on a left side of a patient's head or neck and the second sensor 3b can be configured for being positioned on a right side of the patient's head or neck (e.g. a side of the patient's head or neck that is opposite the side of the patient's head or neck to which the first sensor 3a is positioned). For instance, in some embodiments the first sensor 3a may be positioned on the left side of the patient's head, the left side of the patient's head behind the patient's left ear, or on the left side of the patient's forehead or on the left side of the patient's neck. The second sensor 3b can be positioned on the right side of the patient's head, the right side of the patient's head behind the patient's right ear, on the right side of the patient's forehead or on the right side of the patient's neck.

The sensors can be configured and/or positioned to detect the patient's brain reaction to the evoked potential transmitted to the patient's nervous system via the evoked electrodes. For instance, the sensors can be positioned and/or configured to detect the patient's brain's reactivity to the evoked potential. For instance, the sensor can detect and/or measure the reaction of the patient's somatosensory cortex, associated sensory cortex, medial lemniscus and/or the thalamus to the evoked potential transmitted to the patient's body via the evoked electrodes.

Figure 7:
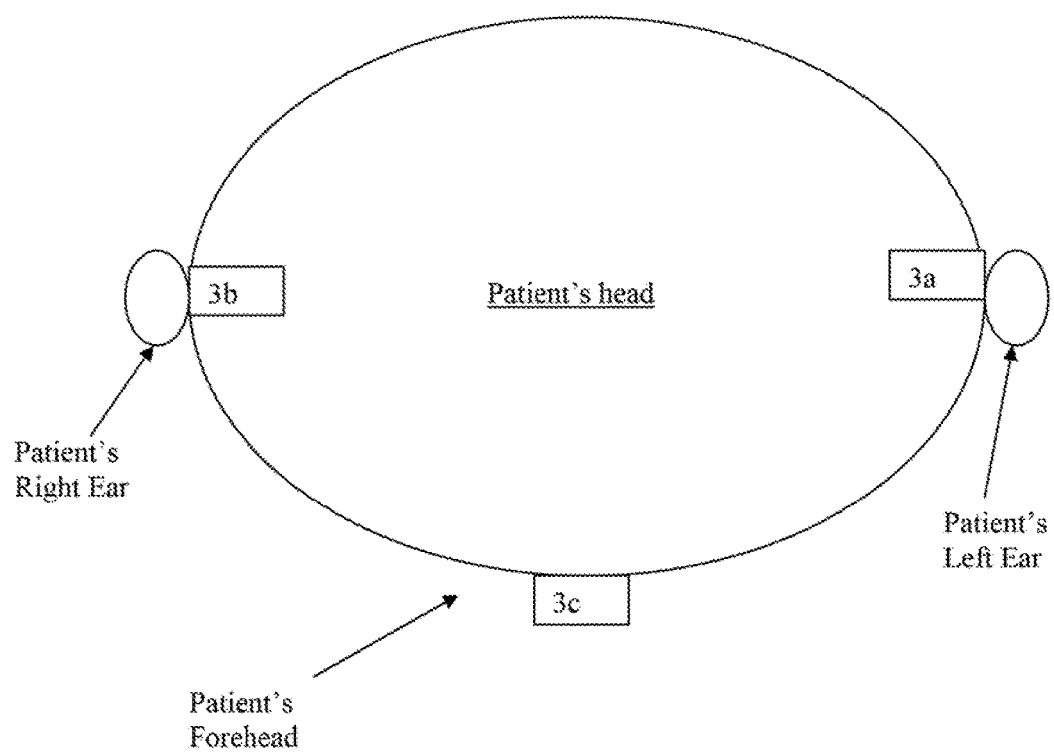
FIG. 7 is a top schematic view of a third sensor 3c configured as a reference sensor that is positioned in a central region of a patient's forehead between a first sensor 3a that is positioned on a left side of the patient's head and a second sensor 3b that is positioned on a right side of the patient's head.

The third sensor 3c can be configured as a reference sensor and may be positioned anywhere on the patient's body. In some embodiments, the third sensor may be positioned between the first and second sensors 3a, 3b to provide a more reliable reference signal as compared to other locations. For instance, the third sensor 3c may be positioned on or near the center of the patient's forehead as shown schematically in FIG. 7, the top of the patient's head, the center of the back or front of the patient's neck (e.g. between the first and second cervical vertebrae), or other location on the patient's body. In some embodiments, the third sensor 3c can be positioned an equidistant distance from the first and second sensors 3a, 3b. In other embodiments, the third sensor 3c can be configured to be positioned less specifically between the first and second sensors 3a, 3b so that the precision of placement of the third sensor 3c between the first and second sensors 3a, 3b is not necessary.

In some contemplated embodiments, the first sensor 3a can be positioned on a left side of a patient and the second sensor 3b can be positioned on the right side of the patient and be configured to function as a reference to eliminate the need for a third reference sensor.

Figure 2:
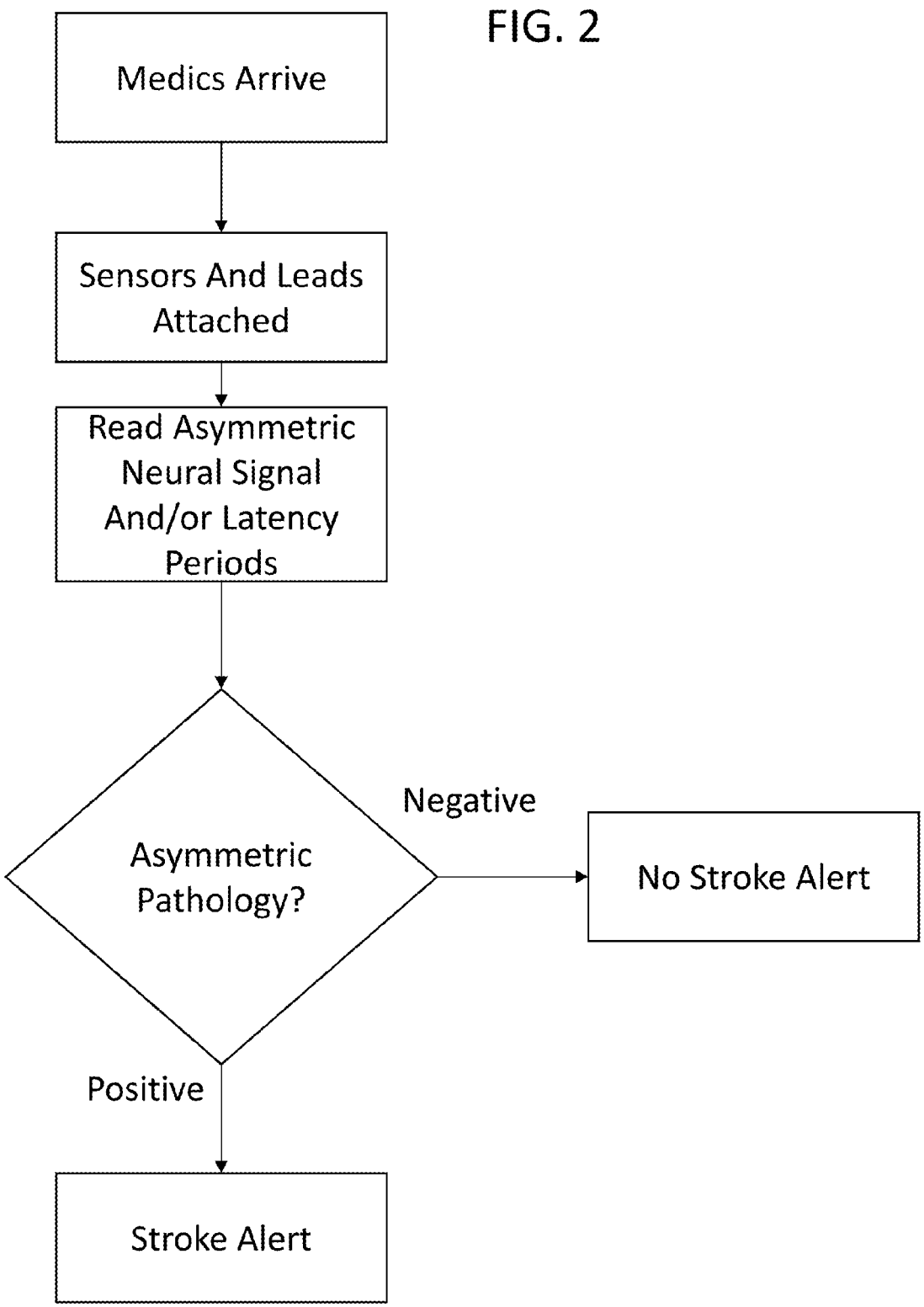
FIG. 2 is a flow chart illustrating a first exemplary method of using neurological condition detection unit.

Embodiments of the stroke detection device can be utilized in methods of treating patients. For instance, the stroke detection device can be used by medics (e.g. EMS personnel, EMT personnel, paramedics, etc.), during emergency care situations. FIG. 2 illustrates one example of such a method.

In some embodiments of the method, medics may travel to a location in which a patient needs help in a vehicle such as an ambulance, a truck, a van, or a car. Once at the location, a medic may find the patient who needs help, such as providing some type of care to the patient at the location. The medic may also transport the patient to a hospital to receive care in a facility having certain equipment needed to provide more substantial care to treat a problem affecting the patient. As part of treating that patient prior to delivering the patient to a hospital, the medic may place evoked electrodes on the wrists, ankles or behind the knees of the patient (e.g. place first and second evoked electrodes 5a and 5b and any other additional evoked electrodes (e.g. third evoked electrode on right side of patient body, fourth evoked electrode on left side of patient's body, etc.) on the patient). For instance, the first evoked electrode 5a can be positioned on the patient's right wrist, right ankle, or behind the patient's right knee and the second electrode 5b can be positioned on the patient's left wrist, left ankle, or behind the patient's left knee. This may be accomplished by use of straps that have interconnectable end portions together. For example, each of the evoked electrodes may be attached to a strap having a plurality of hooks on one end portion and a plurality of loops on an opposite ends for releaseably connecting the end portions together to form a ring or annular shaped strap that is sufficient to encircle a patient's wrist, ankle, or leg to position the evoked electrode in contact with the skin of the patient at such a location. It is contemplated that a type of adhesive material or a gel could also be applied between the electrode and the patient's skin by the medic to facilitate adhesion and/or positioning of the evoked electrode on the patient and/or efficient functioning of the evoked electrode when used on the patient.

The medic may also position the first, second, and third sensors 3a, 3b, and 3c and/or any other sensors of the stroke detection device on to the patient's body. For instance, the medic may position the first sensor 3a on the right side of the patient's forehead, behind the right ear of the patient, or on the right side of the neck of the patient. The medic may position the second sensor 3b on the left side of the patient's forehead, behind the left ear of the patient, or on the left side of the neck of the patient. The third sensor 3c may then be positioned on the patient between the first and second sensors 3a, 3b, such as in the middle of the patient's forehead, on the back of the patient's neck, or on the top of the patient's head. For some embodiments having more than three sensors, these additional sensors may also be positioned on the patient.

In some embodiments of the method, the first, second, and third sensors (and any other additional sensors) may be attached to a headband element or a strap that may be positioned around a patient's head so that the first, second, and third sensors 3a-3c are all positioned at the same time when the headband, helmet, or other type of head gear is positioned on the patient. As another alternative, an adjustable collar that may be adjustably tightened around a user's head or neck can be positioned on the user to position the first, second, and third sensors (and any additional sensors) on the patient at the same time. Adhesive, a gel, or other type of material may be placed on each sensor to help position the sensor on the patient at a desired location. For example, each sensor may be included in a patch having an adhesive on it so that each sensor may be positioned in contact with a patient's skin at a desired location. For embodiments in which the sensors are included in a type of garment that can be worn by a patient, the headband, a helmet, a collar, or other type of garment or headgear that may include one or more of the sensors can also include such patches or other type of adhesive to facilitate positioning of the sensors.

The evoked electrodes and sensors may be placed on the patient in any particular order or arrangement as desired by at least one medic. For instance, the sensors may all be positioned before or after the evoked electrodes are positions. As another example, the sensors may be positioned after at least some of the evoked electrodes are positioned on the patient or the sensors and evoked electrodes may be positioned on the patient at the same time by multiple medics or only one medic.

The medic may position the evoked electrodes and sensors on the patient prior to placing the patient in an ambulance or other vehicle. Alternatively, the medic may wait until the patient is in an ambulance or other vehicle before positioning the electrodes and/or sensors. As yet another alternative, some of the sensors and/or electrodes may be placed on the patient before the patient is placed in a vehicle and others may be positioned after the patient is positioned in the vehicle for transport to a hospital or other type of care facility.

Figure 6:
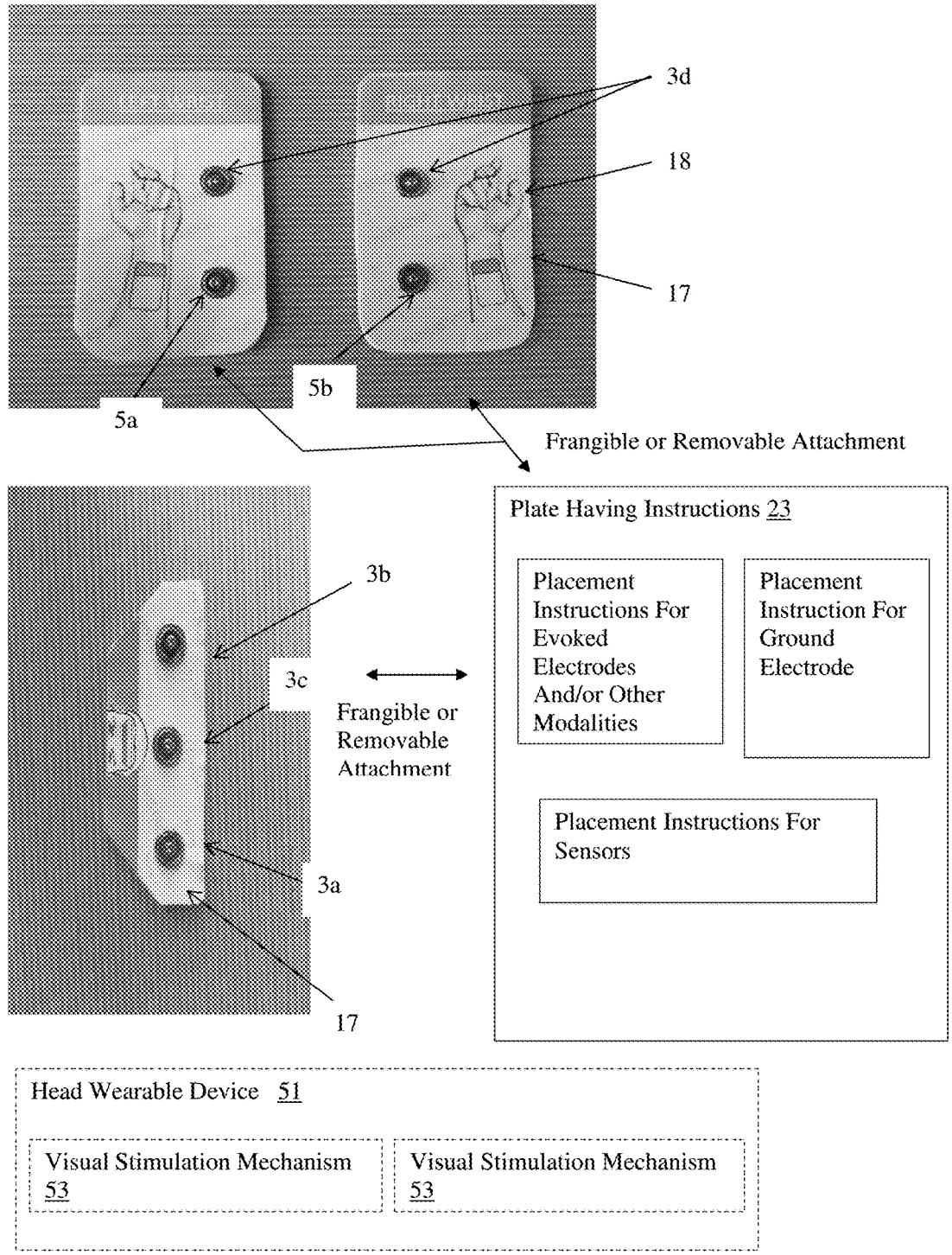
FIG. 6 is a perspective view of a sensor and electrode kit having electrodes and sensors for positioning on a patient that may be utilized in the first exemplary embodiment of the neurological condition detection unit. An optional head wearable component of the kit having visual stimulation mechanisms is shown in broken line in FIG. 6.

An exemplary embodiment of evoked electrodes and sensors that may be provided in a kit with an embodiment of the neurological condition unit is shown in FIG. 6. The evoked electrodes and sensors may be provided in a kit form that includes a plate or paper having instructions for positioning of the evoked electrodes and sensors. The kit can be configured to include the instructions, sensors, and evoked electrodes in a single plastic bag that contains these elements of the kit. The single bag may be a sealed vacuum bag that is sealed after the elements of the kit are positioned in the bag. The evoked electrodes and sensors may be positioned on pads or other structure that is adhesively coupled to the member having the instructions or is frangibly positioned on that member so that these elements may be peeled from the member or broken off from the member for placement on a patient for a one-time only use of the electrodes and sensors. After the electrodes and sensors are used on a patient and these elements may be thrown away and a new kit having the same elements can be used for a new patient. As an alternative, the elements of a kit may be re-used for multiple patients instead of being designed for use as a one-time only use.

The kit may include, for example, left and right evoked electrode pads 17 (e.g. first and second pads each connected to at least one evoked electrode) for being adhesively attached to the skin of a patient near the patient's right wrist and left wrist. A removable covering 18 can be positioned on the side of each pad having the adhesive to cover the adhesive so that the pad is only attachable near a patient's wrist after the covering 18 is removed to expose the adhesive layer on the pad 17. Indicia providing instructions on where each pad should be positioned on a patient can also be included on the covering 18 and/or on other instructions 23 provided with the kit, such as instructions placed on a plate or other member to which the pads 17 of the kit may be removably attachable. The instructions can include one or more schematics or drawings to illustrate how each pad should be positioned on a patient.

At least two pads 17 can each include at least one respective evoked electrode (e.g. first evoked electrode 5a or second evoked electrode 5b). One or more fourth sensors 3d can also be included in each pad. The one or more fourth sensors 3d can include an accelerometer, a temperature sensor that measures the temperature of the patient, a light emitting diode (LED) sensor for detecting skin color and/or skin friability, a positional sensor and/or a perspiration sensor. A LED that is configured to blink the light of the light emitting diode or keep that light on in response to a determination that the pad is incorrectly positioned on a patient can also be included. The positioning determination can be made based on a detection made by a fourth sensor that is connected to the light emitting diode. For instance, the one or more fourth sensors can include a positional sensor that detects the distance that sensor is from another positional sensor of another pad having an evoked electrode so that when the detected distance is smaller than a pre-selected threshold, the light of the light emitting diode is activated to blink or stay on to indicate the position of the evoked electrodes provided via the pads is not correct. The positional sensor can also send data to the computer device to identify the incorrect positioning of evoked electrodes so that the computer device can use that information to control for latency that may exist in the measurement results due to the misplacement of the evoked electrodes. The perspiration sensor can be configured to provide measurement data to the computer device to detect sweat from the patient for use in calibrating the measurement results received from other sensors.

The light emitting diode (LED) sensor for detecting skin color and/or skin friability can be configured to provide measurement data to the computer device 1 to provide initial inputs for the age and race of a patient. That measurement data can be overwritten by input provided by a user who may enter the age and race of the patient via an input device as the user entered data could be more accurate than the LED sensor data. But, if no such user input is provided, the LED sensor data can be used to help improve the accuracy of the device as it assesses measurement data received from the sensors for use in assessing the patient's condition.

The light emitting diode (LED) sensor for detecting skin color and/or skin friability that may be one of the one or more fourth sensors 3d can be configured so that the sensor includes an LED that may use either infrared or non-infrared light that is paired with a photodiode. The photodiode may be configured to measure the light emitted from the LED that is reflected off of a patient's skin back to the photodiode that is positioned on the pad 17 or other element that is used to position the LED sensor on the patient. The amount of light measured to have been reflected back to the photodiode can be measured as light that was not absorbed or scattered by the patient's skin. This measurement data can be used to reference ranges of data stored in memory of the computer device that identifies the skin color of the patient. For instance, if the measurement data is within a first range that is identified as corresponding to Caucasian or white, the computer device may be configured to receive the measurement data of the fourth sensor and determine that the patient is Caucasian or white. If the measurement data is within a second range that is identified as corresponding to African American or black, the computer device may be configured to receive the measurement data of the fourth sensor and determine that the patient is African American or black. If the measurement data is within a third range that is identified as corresponding to Asian or Indian, the computer device may be configured to receive the measurement data of the fourth sensor and determine that the patient is Asian or Indian.

The same measurement data from the photodiode may also be compared to other stored data that corresponds to age ranges for a patient so that the computer device can be configured to estimate an age of the patient based on the fourth sensor measurement data. For instance, if the measurement data is within a first range that is identified as corresponding to 40-50 years old, the computer device may be configured to receive the measurement data of the fourth sensor and determine that the patient is 40-50 years old. If the measurement data is within a second range that is identified as corresponding to a patient having an age of 50-60 years old, the computer device may be configured to receive the measurement data of the fourth sensor and determine that the patient is 50-60 years old. If the measurement data is within a third range that is identified as corresponding to 60-70 years old, the computer device may be configured to receive the measurement data of the fourth sensor and determine that the patient is 60-70 years old.

In some embodiments, it is contemplated that the pre-selected measurement ranges may be stored in non-transitory memory of the computer device or memory that is accessible to the computer device so that the pre-selected ranges are based on age and race such that the measurement data can be used to determines both age and race of a patient by comparison of that data to this single set of stored age and race range data. As another alternative, the pre-selected age and race ranges may be stored as separate sets of data so that the same measurement data is used to identify the age based on pre-selected and saved first set of age data ranges and also used to identify race based on a different second set of pre-selected and saved race related range data If an accelerometer is included as sensor of the pad 17, the accelerometer may be configured to send measurement data to the computer device 1 to provide a feedback loop for electric current delivered for stimulation to the patient via the one or more evoked electrodes of that pad. The electric current and/or voltage may be continued to be increased for each shock to a patient provided via an evoked electrode until the accelerometer detects a movement of a patient's wrist or arm to which the pad 17 is attached that is at or beyond a pre-selected threshold (e.g. acceleration, velocity, and/or distance the accelerometer moved relative to a pre-selected threshold such as a movement of 10 cm, movement of 5 cm, movement of 2 cm, movement of 10-2 mm, etc.). The measurement data that identifies the amount of a movement of the patient's hand or arm measured by the accelerometer can also be used by the computer device to correlate how much power was induced via the evoked electrodes into the patient to provide a shock to the patient. Such data can also be used by the computer device to determine whether that evoked electrode is properly positioned on the patient's body.

The measurement data from the accelerometer sensor, which can be one of the one or more fourth sensors 3d, can also be used by the computer device to determine a level of noise that may be included in the patient's shock response measurement data from motion of the patient and/or to determine whether an evoked electrode of the pad or other body wearing element to which that accelerometer is attached is properly positioned. For instance, motion of a patient above a set threshold may be correlated with a pre-selected and saved noise error correction factor data set stored in the memory of the computer device. The accelerometer measurement data may be used by the computer device to compare that data to the noise error data so that a noise error corrective factor is selected for evaluating other sensor measurement data based on a noise error associated with detected motion of the patient. Alternatively, the computer device may be configured to not use any measurement data that is collected from a patient's response to one or more shocks when the accelerometer measurement data indicates the patient was moving during the testing of the patient so that data is not utilized by the computer device to detect a patient's condition that may be too error-prone to allow for an accurate determination of the patient's neurological condition.

A third pad 17 can also be connected to first, second, and third sensors 3a, 3b, and 3c for positioning on a patient. For example, the third pad can have a covering 18 over an adhesive portion of the pad that is removable to facilitate adhesive attachment of the third pad to the back of a patient's neck, forehead of a patient, or other portion of a patient's body. In embodiments where the pads are attached to a member in a bag of the kit, the covering 18 may be a portion of the member to which the pad is removably attached. The third pad can also include an infrared sensor that is configured to measure oxygen content of the blood near the surface of the patient's skull. Alternatively, a fourth pad can be provided that has such an oxygen content sensor.

The first, second, and third sensors as well as any fourth sensors 3d can each be configured as electrodes or other type of sensor that is able to convert a measurement signal from analog to digital data and subsequently wirelessly transmit the converted digital measurement data to the computer device 1 via a wireless communication link (e.g. Bluetooth, etc.). In other embodiments, the sensors may be wired to the computer device 1 to provide the communication connection.

In some embodiments of the kit, pads 17 to which evoked electrodes are attached may be sewn into gloves so that each glove has at least one pad 17 having one or more evoked electrodes and at least one fourth sensor 3*d*. Each glove can be configured to cover a patient's hand and extend up the patient's forearm to a desired stimulation site at which the pad 17 of the glove is positioned when the glove is worn by a patient. Each glove can have a line defined therein or drawn thereon, printed thereon, or otherwise demarcated thereon so that a medic could determine by referencing that line whether the glove was twisted when it was put on the patient. If the glove was determined to be twisted by referencing that line of the glove, the medic could readjust the glove to prevent such twisting to avoid the twisting providing less accurate results. For example, if one glove was twisted sufficiently while the other glove was not twisted, the left and right stimulation amplitudes could differ due to that twisting, which could result in inaccurate responses measured by the first and second sensors 3*a* and 3*b*. A stretch center sewn into the glove can be used to help a user detect twisting and help prevent such inaccurate measurements by untwisting any twisted glove before the device evokes response from a patient or measures those responses.

In other embodiments of the kit, pads 17 to which evoked electrodes are attached may be sewn into or otherwise incorporated into arm bands so that each arm band has at least one pad 17 having one or more evoked electrodes and at least one fourth sensor 3*d*. For instance, each arm band may be an annular shaped pad 17 that is made of an elastomeric material that has an inner channel through which a patient's arm can be passed so that the user may wear the arm band on the user's forearm. The elastomeric material of the arm band can be configured to ensure the annular shaped pad 17 is tightly and/or compressively fit against the patient's arm so that the evoked electrode and one or more fourth sensors of the arm band are positioned on the patient's skin of the patient's forearm or otherwise in sufficient engagement with the patient's skin of the patient's forearm. Embodiments of the arm band for the pads 17 can be configured to include a marking or other indicia (e.g. a centerline or other type of indicia) that can be configured to indicate to a medic or other type of care provider that the arm band is being worn by a patient correctly for the sending of shocks to the patient via the one or more evoked electrodes of that armband and for the one or more fourth sensors 3*d* to be able to accurately measure data relating to the patient's responses to those shocks. The indicia can be configured to allow for a visual inspection to verify the arm bands are being worn on the right and left arms of a patient correctly before the computer device is used to assess a condition of the patient to help ensure the results of the conducted assessment are accurate.

After the sensors and evoked electrodes and sensors are positioned on the patient via the pads 17 (e.g. pads adhesively attachable to a patient, arm bands, gloves, etc.) or other positioning mechanisms, the computer device may be activated and/or input may be provided to the computer device 1 to initiate monitoring of the patient's condition to detect whether the patient has experienced a stroke, is experiencing a stroke, or may be about to experience a stroke. An electrical current can be periodically transmitted to the patient via the evoked electrodes (e.g. first and second evoked electrodes 5*a*, 5*b* and/or any additional evoked electrodes that may be included in a particular embodiment). For instance, the electrodes may transmit a current of 5 mA, a current of over 50 mA, a current of between 50 mA and 200 mA, a current not greater than 200 mA, or another current within a pre-selected value range or at a pre-selected value, to the left and right sides of the patient via the first and second evoked electrodes 5*a*, 5*b* to evoke a response to this current from the nerves of the patient. The current may "shock" the patient and may be transmitted for a first pre-selected period of time such as for less than 1 second, less than 0.5 seconds, less than 0.25 seconds, or other pre-defined time period. Multiple "shocks" may be provided to the patient within a given time period. For instance, the patient may experience 2-3 evoked potential events (e.g. shocks), 2-5 evoked potential events (e.g. shocks), 4-5 evoked potential events, or more than five evoked potential events (e.g. shocks), each second by receiving the current for the pre-selected time period multiple times within a second. After each evoked potential event (e.g. shock), the current may cease being transmitted to the patient for a second pre-selected time period before the next evoked potential event (e.g. shock) is applied to the patient via the evoked electrodes and electricity transmitter unit 1*g*.

The evoked electrodes may alternatively be replaced by or supplemented with other stimulating evoked electrodes or other modalities connected to the computer device for actuation of visual stimulus to be provided to a patient. For instance, modalities can be configured to provide a visual evoked potential to a patient. An example of such modalities are may be one or more light emitting devices or other type of visual stimulation mechanisms 53 that provide visual stimulation to a patient via a form factor of a portable light. For instance, instead of pads, or an armband, a head wearable device 51 such as a headband, goggles, glasses, or another type of headgear can be worn by a user and have evoked electrodes that are configured to provide visual stimulation to the left and right eyes of a patient. The evoked potential may provide visual stimuli to a patient via flashing of light of a sufficient quality to stimulate a patient sufficiently to evaluate the patient's neurological condition from the patient's response to the visual stimulus. The flashing light may be the stimulus provided to the patient via these visual stimulation mechanisms 53. The computer device can be configured to provide power to the visual stimulation mechanisms 53 so that the duration and brightness of the light emitted to evoke a response from the patient is provided to the patient to provide a pre-selected number of visual stimuli to the patient within a pre-selected time period. These visual stimuli can be provided as an alternative to electrical shocks or may be provided in combination with the electrical shocks via other evoked electrodes (e.g. evoked electrodes positioned by wrists of a user wearing arm bands, gloves, or pads having such evoked electrodes, etc.).

The neural signals of the patient's brain (e.g. the electrical potentials of the patient's brain or the biosignals of the patient's brain) may be read by the computer device by use of the sensors to determine whether there is an asymmetric pathology. For instance, if there is determined to be an asymmetric pathology such that one side of the patient's brain (e.g. the right side or left side of the patient's brain) has a substantially different somatosensory evoked potential (SEP) as compared to the opposite side of the patient's brain (e.g. the other side of the right or left side of the patient's brain), then the computer device 1 may be configured to generate an alert to communicate the alert to the medic to identify the detected stroke condition to the medic via one or more output devices and/or input/output devices. If there is no difference in SEP response or a difference is not outside of a pre-selected threshold range, then the computer device 1 may be configured so that a stroke event is not detected and no such alert may be provided.

It is also contemplated that the computer device can be configured so that motor evoked potential, sound/aural evoked potential and/or visual evoked potential are also utilized by the computer device to determine whether an asymmetric pathology may be present in a patient. For instance, different devices, input/output devices, sensors and/or detectors may be connected to the device to transmit motor evoked potential, sound/aural evoked potential and/or visual evoked potential for use in evaluating the patient's response to these evoked events.

In other embodiments of the method, the stroke detection device can be configured for use in urgent care facilities, general practitioner doctor offices, nursing homes or assisted living environments in which nursing staff or other staff members having a limited amount of medical training may use the device to help them detect whether a particular person in the care of that facility has experienced a stroke or is undergoing a stroke. To perform such monitoring or detection, the staff personnel may position the evoked electrodes and sensors, connect those evoked electrodes and sensors to the stroke detection device, and thereafter run the device to monitor the condition of the person under their care.

Figure 3:
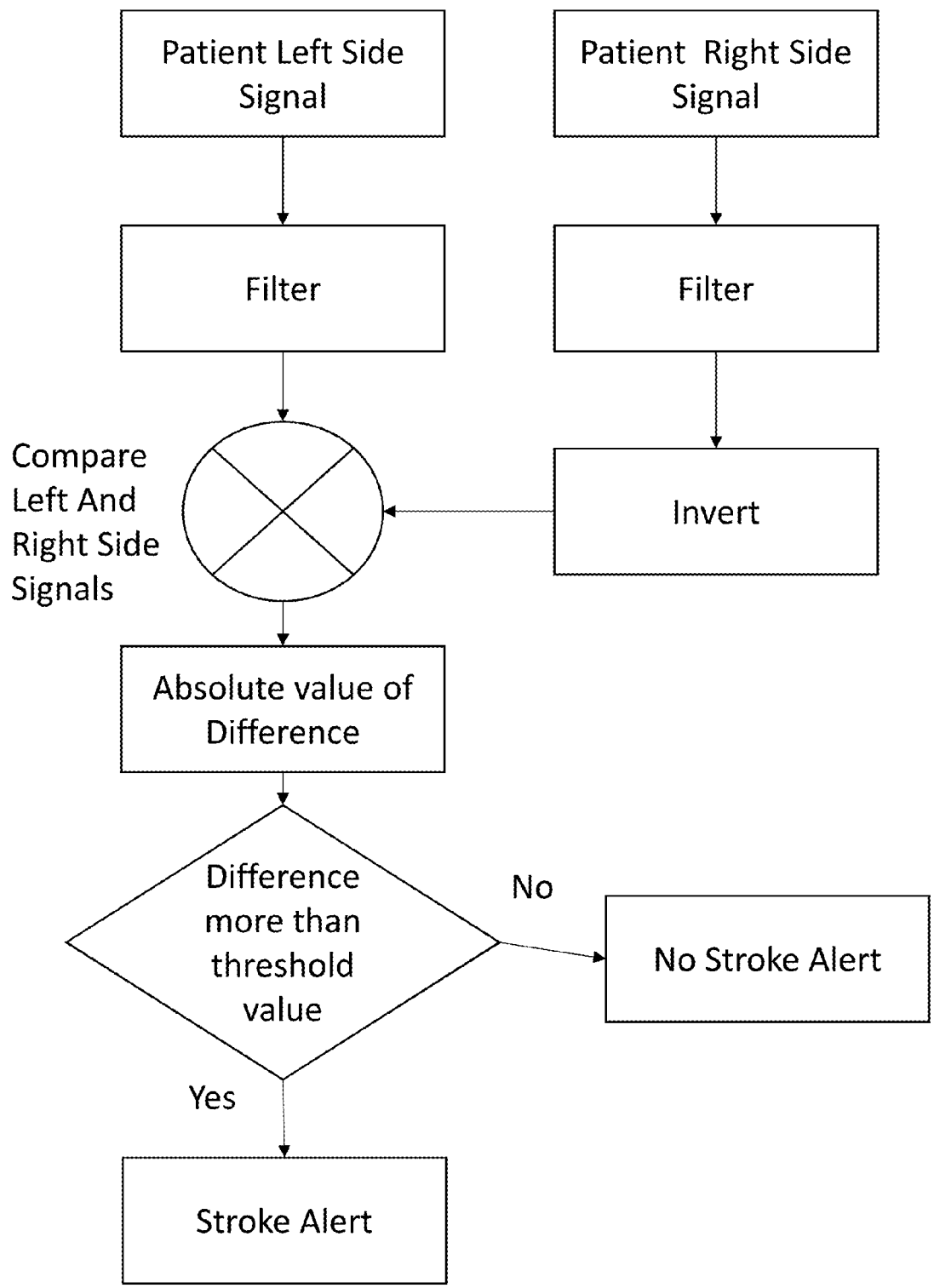
FIG. 3 is a flow chart illustrating an exemplary method by which the first exemplary embodiment of the neurological condition detection unit can be configured to collect and store data for use in assessing whether a patient has experienced a stroke.
Figure 4:
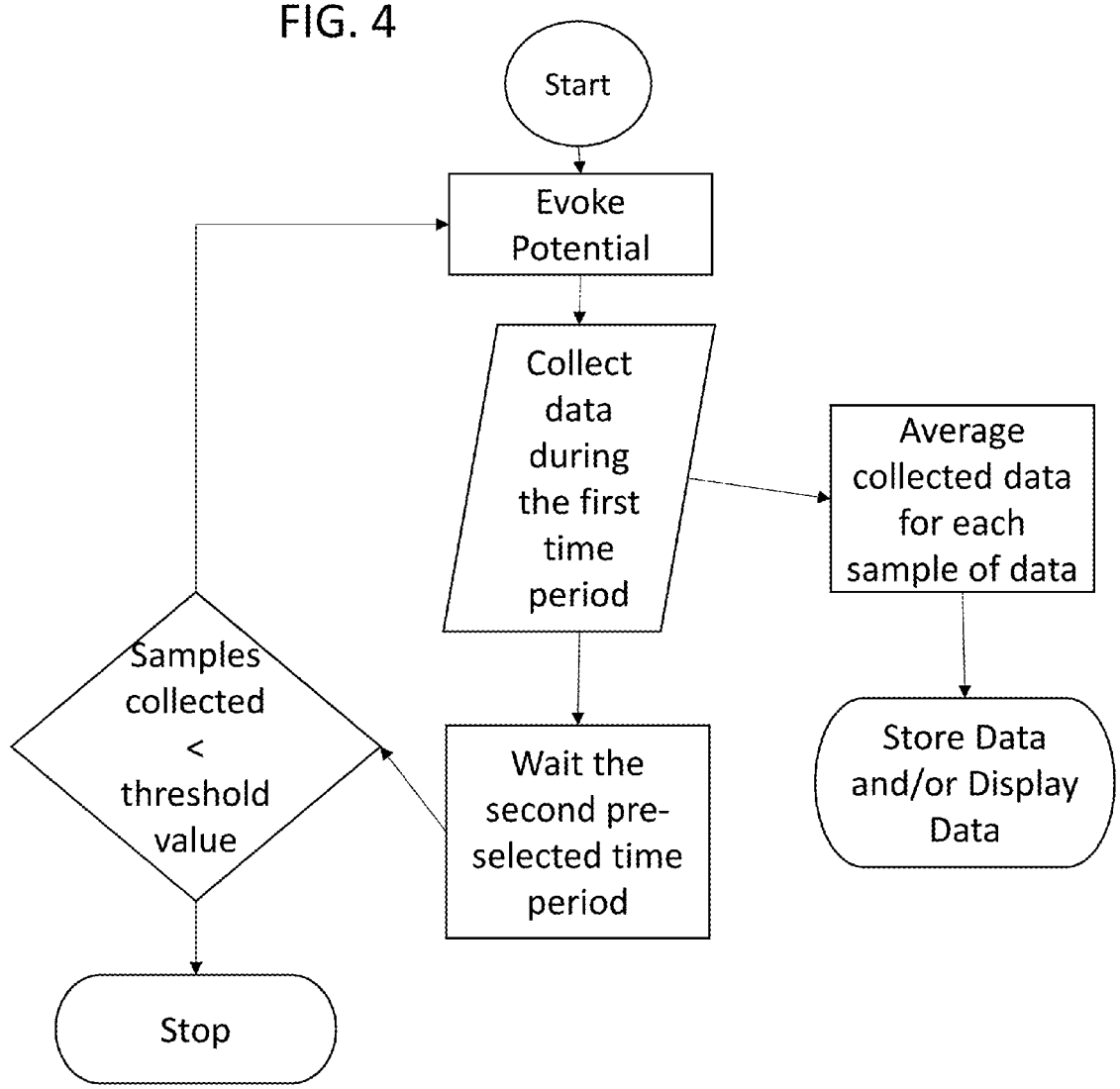
FIG. 4 is flow chart illustrating an exemplary method by which the first exemplary embodiment of the neurological condition detection unit can be configured to detect a stroke based on data collected from a patient responding to at least one evoked event (e.g. at least one electrical shock at a pre-selected electrical current value).
Figure 5:
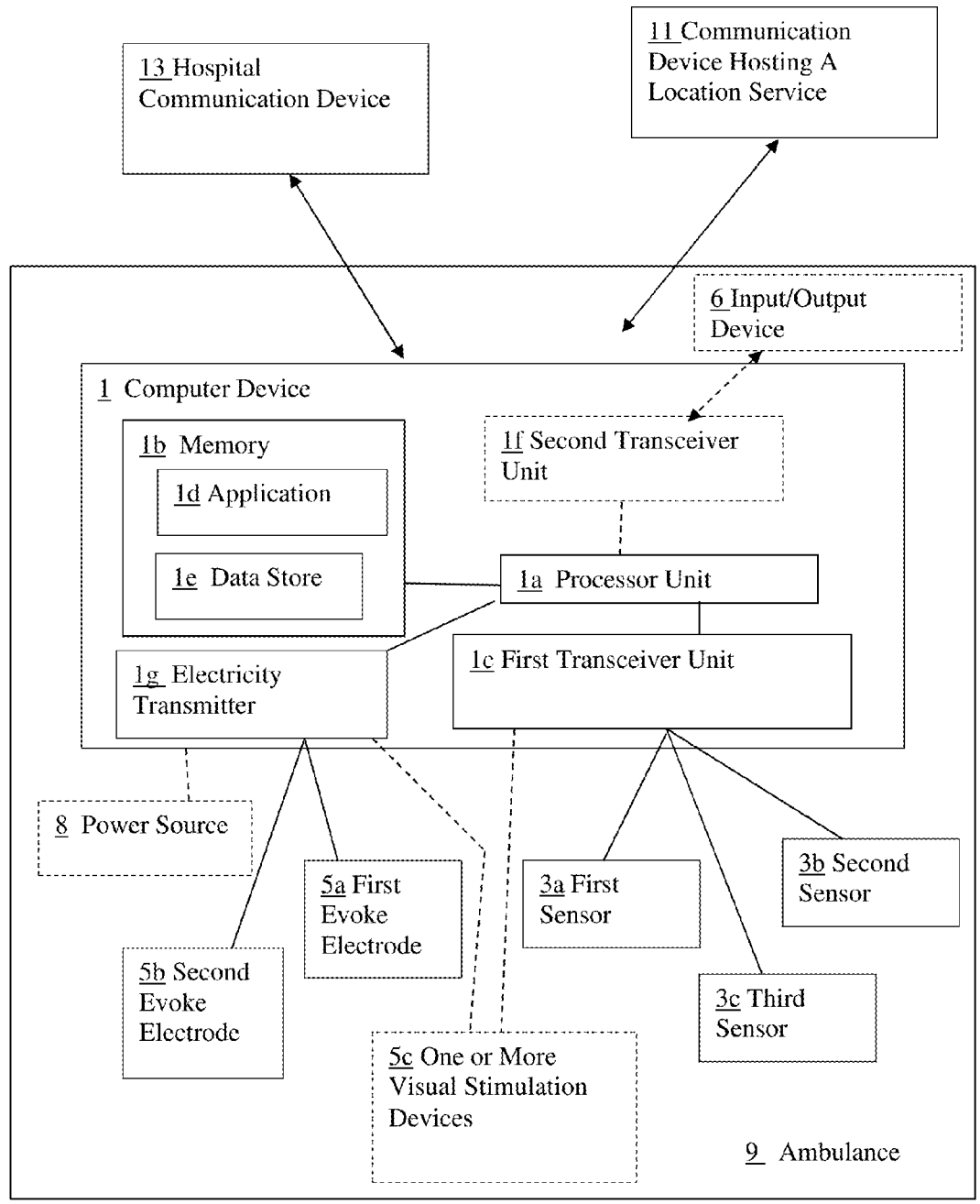
FIG. 5 is a block diagram illustrating the first exemplary embodiment of the neurological condition detection unit in a communication system in which the neurological condition detection unit can be communicatively connected to other remote devices via a network connection (e.g. a wide area network connection or other type of network connection).

Embodiments of the stroke detection device can be configured to collect data from the patient and perform the comparison of SEP data obtained from the patient from the right and left sides of the patient's body in different ways. FIGS. 3 and 4 illustrate one exemplary comparison method that may be utilized by the computer device 1. An application 1d stored in the memory 1b of the computer device may define the method to be performed by the computer device 1 by a processor executing the code of the application 1d to perform this comparison.

The code of the application can be stored in both the device and a central communication server having a processor, non-transitory memory, and at least one transceiver unit that is communicatively connectable to the computer device 1. The code can be updated at the central communication server and this update may subsequently be communicated to the computer device via a network connection (e.g. an internet connection, a cellular network connection, a local area network connection, a wide area network connection, etc.). The central communication server may also be configured to receive data from different devices 1 to use that data to optimize the code of the application so that the application can provide improved performance after being updated. The updates to the application code made at the central communication server can be periodically transmitted to each of the devices that may be employed in different environments so that the devices may update the code for the applications stored in their memory for updating of their applications and improving the performance of the devices 1.

Referring to FIG. 4, the computer device 1 may be configured to begin providing shock treatments, or evoked potential, to the patient after receiving input to initiate stroke detection and/or monitoring for the patient. Such an initiation may occur when the medic selects a button on a graphical user interface displayed to the medic on a display device to provide such input to the computer device. As another example, such initiation of stroke detection and/or stroke monitoring may occur when the computer device 1 detects that the evoked electrodes and sensors are positioned on a patient's body.

An evoked potential may then be transmitted to the patient via the electricity transmitter unit 1g and the evoked electrodes so that the left and right sides of the patient's body near corresponding left and right side nerves of the patient's body each receive the same amount of current for the same amount of time (e.g. current of 5 mA for less than 0.5 seconds or current of no greater than 200 mA for less than 0.75 or 0.25 seconds, etc.) The sensors can collect data from the patient's body at the locations in which the sensors are positioned to collect data about the sensory evoked potential that is generated by the patient's body in response to the evoked potential (e.g. each shock). That collected data is transmitted to the memory 1b of the computer device via the transceiver unit 1c and/or processor unit 1a of the computer device 1 for saving in a data store 1e. The data is collected over at least the first pre-selected time period. This time period may be considered a third preselected time period in some embodiments. The third pre-selected time period may only include time within the first pre-selected time period and/or the second pre-selected time period. For instance, the third pre-selected time period may include a portion of the first pre-selected time period or the entirety of the first pre-selected time period in which the patient's body is experiencing the evoked potential and may also include additional time that may extend into the second pre-selected time period in which the event potential is not being transmitted into the patient's body (e.g. the third pre-selected time period may include time in which the patient is being shocked and may also include time in which the patient has ceased being shocked).

If the number of samples of data collected from the patient is not over a pre-selected threshold value, then the computer device may be configured to cause the electricity transmitter unit 1g to emit electrical current to the evoked electrodes for the first pre-selected time period again and then cease the providing of that current to the patient for the second pre-selected time period so that additional data can be collected by the sensors. The samples of collected data received from the first, second, and third sensors 3a-3c may be stored in the memory of the computer device 1. In some embodiments, the samples of collected data received by the sensors may be averaged or otherwise manipulated by the processor unit 1a prior to storing that data in a data store 1e in the memory 1b. This process of providing evoked potential (e.g. a shock) at separated time intervals by the computer device 1 to collect and store data for assessing the condition of the patient may be repeated until the data that is collected from the sensors 3a-3c is over a threshold value for samples of data.

In some embodiments, the computer device 1 can be configured so that between 128 and 256 samples of SEP data can be collected from the patient. Other embodiments may be configured to collect more samples of data per second or less samples of data from the patient before making a determination on whether the patient may have undergone a stroke or is experiencing a stroke.

The data that is received from each sensor may be stored in a table or other type of database or data store. The data from the first sensor, second sensor, and third sensor may each be assigned to a respective column of a table or otherwise grouped so that data from each sensor is grouped separately from data from the other sensors to facilitate the comparison of data from the different sensors. After sufficient data has been collected from the patient, the data from the first sensor 3a can be compared to the data collected from the second sensor 3b located on an opposite side of the patient's body from the first sensor 3a. An example of how that data may be compared is shown in FIG. 3.

For example, patient left side signal data can be filtered and the patient's right side signal data can also be filtered. The filtration of these data signals may be performed using the same type of filtration methodology. The filtration of the data may be configured to remove noise from the collected data that may be present due to the electrodes or other type of possible interference in the data. After filtration, one of the sets of data can be inverted for purposes of comparing to the other set of data. For instance, the patient's right side signal data can be inverted for comparing to the uninverted filtered patient left side signal data. In other embodiments, the patient left side signal data can be inverted for comparing to the uninverted filtered patient right side signal data. An absolute value of a difference between the right and left side signal data is then determined. Such an absolute difference may identify a difference in disregard of whether the difference is a positive or negative numerical value (e.g. −5 and +5 are treated the same way). If the difference between the right and left side patient signal data is below a threshold value, the computer device 1 can be configured to determine that the patient has not undergone a stroke or is not undergoing a stroke so that no stroke alert is generated to communicate a warning to the medic. If the difference between the right and left side patient signal data is at or over the threshold value, the computer device can be configured to determine that the patient has undergone a stroke.

Noise levels can be used by the device to determine a test length for the patient. First and second sensor 3a and 3b can be positioned on the patient prior to providing any stimulation (e.g. shocks/evoked potentials etc.) to the patient to provide measurement data to the device 1 that the device can save and subsequently use to approximate noise levels in the patient's current environment. That data can be used by the device to estimate how many samples it will need to correctly diagnose a neurological condition of the patient and adapt the number of samples to be taken from the patient based on the determined noise level. The number of samples that are needed can be combined with the stimulation rate to communicate to a user via an output device how long the testing of the patient (e.g. evaluation of the patient to be performed by the device) will take prior to the device beginning to initiate stimulation to the patient via the evoked electrodes.

In some embodiments, noise levels can be measured via sensor data so that the computer device is able to determine a baseline noise environment level prior to performing an evaluation of the patient via the shocking or other stimulation of the patient via evoked electrodes. The sensor can provide measurement data used to determine the electromagnetic (EM) noise levels in different environments as well as other noise measurements (e.g. accelerometer related noise concerning patient motion, etc.). The measurement data obtained prior to the testing of the patient can be used by the computer device to perform dynamic environmental filtering so that filters are automatically applied to the measurement data received during testing of a patient in which the patient's responses to shocks are collected from the sensors and subsequently evaluated by the computer device. In some embodiments, one of multiple different pre-selected measurement data evaluation functions may be utilized by a processor of the computer device to perform the analysis of the received measurement data based on the prior determination of the noise level that was determined to exist prior to the testing being started.

For instance, in some embodiments, the data collected from the sensors can be used to generate a wave form or a curve that identifies a response to an SEP of the patient based on the data collected from each sensor. In some embodiments, the wave form or curve can be formed based on electroencephalography (EEG) or electrocorticography (ECoG) principles. Each wave form or curve for corresponding time periods between the first and second sensors 3a, 3b can be compared to each other to determine a difference between the amplitude positions of the wave forms at corresponding times (e.g. the difference in amplitude of a signal from the right side of the patient's body as compared to the left side of the patient's body at the same time at which the data was recorded) or evaluate other morphological features of measurement data of the response of the user to the shocks or other stimulation that may be provided via evoked electrodes. If the difference in amplitude positions is greater than or equal to a pre-selected threshold value, then the computer device can be configured to detect the patient as having experienced a stroke or undergoing a stroke for generation of a stroke alert for communicating the stroke alert to a medic.

To perform the comparison of the patient's left and right side signals, the application 1d can define a pattern recognition methodology used by the processor to evaluate the stored data collected from the sensors, a peak detection methodology used to detect a peak of a waveform of a EEG signal for the data obtained from the sensors 3a-3c, and an amplitude comparator methodology for comparing the absolute differences in amplitude that may exist for that data collected from each sensor. This methodology may incorporate a wave construction technique that is configured to provide wave sorting or spike sorting to differentiate different waves to avoid wave conglomeration to improve the accuracy of the amplitude comparisons being made by the computer device. The application can also be configured so that latency that may exist for data from one sensor as compared to other sensors can be accounted for due to the patient's body structure and/or due to the functioning of the electrical communicative components of the stroke detection device.

For instance, in some embodiments the computer device can be configured to perform an evaluation of the measurement data it receives from the sensors. The evaluation of the measurement data can include an evaluation and/or comparison of the subcortical to cortical ratio of the measurement data for the responses of the left and right sides of the body, an evaluation and/or comparison of the absolute amplitudes of the measurement data for the responses of the left and right sides of the body, the first and second derivatives of the measurement data for the responses of the left and right sides of the body, the N35 component of the measurement data for the responses of the left and right sides of the body, the absolute latency of the measurement data for the responses of the left and right sides of the body, the amplitude ratio of the measurement data for the responses of the left and right sides of the body, and/or the interpeak latency of the measurement data for the responses of the left and right sides of the body.

The application 1d can also define how demographic factors or dynamic averaging of measurement data should be performed by the computer device running the application. For instance, input relating to demographic factors that can affect how measurement data from the sensors is evaluated can include sex, age, race, height, and skin impedance of a patient. Such data may be provided by sensors (e.g. one or more fourth sensors $3d$ or other sensors) or by a user providing input via an input device that identified an age, sex, race, skin color, or other data relating to such demographic factors for storage in the memory of the computer device for use during testing of a patient.

In some embodiments, a neck recording electrode (e.g. at least one sensor positioned on a patient's neck via a pad or neck band, etc.) can be configured to allow the computer device to control for a misplacement of one or more evoked electrodes. For example, if a right evoked electrode is placed correctly, but a left evoked electrode is positioned 3 centimeters away from its correct placement, the computer device 1 can be configured to correct the measurement data for the misplaced electrode to automatically account for this incorrect positioning. Alternatively, the computer device can be configured to transmit a warning to a user to provide information to the user to adjust the position of the incorrectly positioned evoked electrode. Such an evaluation may be performed via one or more sensors on a patients neck that measure the signals received by the right and left sides of the body in response to shock events or other stimulations. The latency of the measurements received by the right side can be compared to the left side data via the neck sensor measurement data. When one side of the body is determined to have a latency that is beyond a pre-selected threshold, this can indicate that one of the evoked electrodes is incorrectly positioned. The use of the neck sensor(s) to account for incorrect positioning of one or more evoked electrodes can permit the computer device to avoid making incorrect evaluations due to incorrect placement of the evoked electrodes on a patient.

It is contemplated that neural networks and/or evolutionary selection algorithms and artificial neural networks can be used to generate binary classification functions and/or other discriminant classification patterns for different races, gender, age, height, and baseline noise environments. Such features can permit the computer device to test a patient and account for the demographics of a patient and noise environment of a patient to improve the reliability and accuracy of the computer device's testing of a patient's neurological condition and evaluation of measurement data obtained via that testing.

The computer device can also be configured to utilize dynamic averaging of measurement data based on various factors, such as the noise conditions present during a test of a particular patient. The computer device can be configured so that the number of shocks utilized to measure patient responses to the shocks is dynamically determined to provide a sufficient number of samples (e.g. each shock and response being a separate sample) to evaluate a patient given various applicable conditions that could affect that testing. For example, in some low background noise environments, only 10-20 stimulations (or samples) may be used to obtain sufficient measurement data for storage and evaluation by the computer device for assessing a condition of a patient while in a high noise environment up to 500 stimulations (or samples) may be taken to obtain sufficient measurement data for storage and evaluation by the computer device for assessing a condition of a patient.

In evaluation of measurement data, the measurement data may be evaluated by the computer device to identify various different types of morphological features based on the measurement data received from the sensors. For example, peak amplitude, power, latency, slope, and other morphological features of the measurement data for the patient's response(s) to the stimuli for each sample may be identified and assessed. These morphological characteristics of the measurement data may covary with each other. Morphological covariation of the data can be performed by the computer device to estimate locations of sensor placement on the patient to identify faulty testing that may provide in an unreliable result that should not be used. Upon such a determination being made, a warning may be communicated via an output device to a user so that the patient can be retested after the sensor positions and evoked electrode positions are rechecked to ensure they are correctly positioned on the patient.

For instance, in some embodiments, the computer device can be configured so that when a variance of two or more morphological characteristics are far removed from the known covariance of those characteristics, the conducted test is interpreted as invalid and a warning is issued to the user via an output device. For example, if an amplitude of a peak is known to vary with slop of another peak by a first factor and a first standard deviation in a given test and the variance between these two factors exceeds a pre-selected covariance threshold, then the test can be determined to be invalid by the computer device.

The third sensor $3c$ may be positioned for providing a reference signal. The reference signal data can be used to filter out artifacts created by the body and/or environment.

The stroke detection device can be positioned in an ambulance such as an ambulatory truck, van, bus, helicopter, boat, airplane, or other type of vehicle used by medics to transport patients. In some embodiments, it is contemplated that the computer device 1 can also be configured to communicate the data collected from a patient to a computer system of the hospital to which the patient is delivered so that the collected data can be used by medical staff of that hospital when treating the patient. For instance, the computer device 1 may be configured to transmit the collected data to a hospital communication device 13.

The computer device 1 can also be configured to analyze the sensor data received from the sensors positioned on the patient to differentiate between whether a detected condition is due to a hemorrhagic burst and/or an ischemic artery block for one or more identified arteries and, for each artery determined to be blocked, estimate or otherwise determine an extent to which each identified blocked artery is blocked (e.g. fully blocked, 90% blocked, 75% blocked, etc.). For instance, the device can be configured so that amplitudes in measurement data from at least one of the sensors is below a pre-selected threshold, a hemorrhage may be detected. In the event major peaks are determined to exist in the amplitudes of the measurement data that are sufficiently below that pre-selected threshold the device may be configured to detect an ischemic artery block and estimate the degree of blockage based on the amplitude levels of the sensor measurement data. In some embodiments, the measurement of the amount of diffusion due to hemorrhagic stroke by use of a far field effects can be used. An abnormal attenuation of signal between two or more points on the brain from such measurement can be indicative of a hemorrhagic stroke and the computer device can be configured to identify such an occurrence via sensors providing measurement data providing data that indicates such an occurrence exists. This information can also be communicated to the hospital communication device 13 to help facilitate the providing of care to the patient when the patient is delivered to the hospital.

The computer device can also be configured to communicate with a location service. For instance, the computer device 1 may be configured to communicate with a communication device hosting a location service 11 (e.g. a workstation or server that hosts a service via a network connection). Such a location service may include a global positioning system related location service or a navigational location service that may be hosted by a communication system. The location data of the computer device 1 can be determined from the location service and the location of certain hospitals near that location can then be determined by the computer device 1. The computer device 1 can use such information so that when a stroke is detected by the stroke detection device, the alert generated by the computer device for being output to the medic can also identify a particular hospital located relatively near the computer device (and thus, the patient and medic) that may be best equipped to treat a stroke condition as compared to other nearby hospitals. The alert may be output to the medic via a display located in a rear of the vehicle in which a patient may be positioned for transport. The alert or other alert related information can also be communicated to a display device, speaker, or other output device that may be positioned by the steering wheel, driver seat, or passenger seat of the vehicle (e.g. ambulance) to communicate such information to the driver or pilot of the vehicle.

It is contemplated that embodiments of the stroke detection device can also be configured to detect other conditions of a patient. For example, embodiments of the device may be configured to detect whether a patient has scoliosis and/or a chronic condition relating to nerve damage and/or peripheral nerve damage. As another example, the device can also be configured to detect whether the patient has experienced an injury to a part of his or her nervous system. The detection of such a condition can be used to provide data to a care provider (e.g. a medic or doctor) and/or may also be used by the computer device to calibrate to the altered physiology that exists when such a condition is detected as occurring to help the device avoid making a false positive detection. As yet another example, embodiments of the stroke detection device can be configured to determine whether a patient has undergone or is undergoing one or more types of nervous system related injuries and/or diseases.

The computer device can also be configured to account for different end user requirements and a tolerance for false positives that may exist for a given care provider. For instance, transport to initial care facilities may not tolerate false negatives to a higher degree than a care provider who has a CT scanner present that may be used to evaluate a patient condition for a patient that has not recently undergone a traumatic event. The computer device can be configured to account for such tolerance chances so that the probability of a false negative is adjusted for a given end user. Input parameters that may be provided via an input device to the computer device can be used by the computer device to determine the sensitivity of the evaluation of measurement data it may perform based on sensitivity, specificity, positive predictive value, and negative predictive value parameters as well as other parameters a user may provide input on for use in account for various cost/benefit options available to a particular end user and health care services that end user may provide.

Embodiments of the computer device can also be configured to utilize machine learning techniques to continually update and optimize how the measurement data is evaluated for sub-segments of a population of patients that may have undergone a stroke or other neurological condition. The computer device may start with a sample of a pre-selected number of patients (e.g. 100, 200, 300, etc.) and optimize its measurement data evaluation methodology based on testing results that it saves in its memory as more patients are evaluated by the computer device. The evaluation optimization process can be based on the stored data from prior tests to provide changes to different pre-selected variables that are used to assess different patients having different demographics (e.g. black men over 80 who are under 6 feet tall, white females under 60 who are between five and six feet tall, etc.). In some embodiments, multiple computer devices employed in different care environments may communicate the measurement data and evaluation data from prior testing of patients to a central server via at least one communication connection (e.g. a network connection, an internet connection, etc.). The central server may evaluate that data and update various variables used by the applications of those computer devices for evaluating measurement data. The updated application variables may then be communicated to the communication devices so that the application of the devices can be updated so that subsequent testing of patients performed by the computer devices utilized the updated evaluation methodology and updated variable information communicated by the central server.

It should be understood that embodiments of the neurological condition detection unit can be configured to meet different sets of design criteria. For instance, in some embodiments the computer device 1 may be incorporated into an electrocardiogram machine, which may also be referred to as an ECG machine or an EKG machine. Such a device may be configured to both provide electrocardiogram sensing and recording for a patient in addition to providing stroke detection services. As another example, the computer device can be configured so that the difference in slope or difference in frequency of the wave forms generated from the sensor data for the patient left and right sides is compared to each other to determine whether a sufficiently significant difference between the slopes of the wave forms at corresponding times exceeds a threshold to detect the occurrence of a stroke. As yet another example, in some embodiments the neurological condition detection unit can be configured to be a modular mobile device that is moveable into and out of different vehicles while other embodiments may be designed to be incorporated into the structure of an ambulance or other type of vehicle. As yet another example, in some embodiment the electricity transmitter unit 1g may be a separate device that is communicatively connected to the processor unit 1a of the computer device 1 and is actuated by the computer device 1 to transmit evoked potential (e.g. a shock) to the patient periodically based on communications received from the processor 1a of the computer device 1. As yet another example, the neurological condition detection unit can include more than three sensors and/or more than two evoked electrodes, multiple different types of input devices and/or output devices and/or multiple different types of transceiver units. In yet other embodiments, the computer device may only use one input/output device for providing output and allowing a user to communicate input and no additional or separate output or input devices. In such embodiments, such an input/output device may be an electronic tablet, smart phone, touch screen display, or other type of input/output device Therefore it should be understood that while certain exemplary embodiments of the stroke detection device and methods of making and using the same have been discussed and illustrated herein, it is to be distinctly understood that the invention is not limited thereto but may be otherwise variously embodied and practiced within the scope of the following claims.

What is claimed is:

1. A method for detecting a neurological condition comprising:
    attaching evoked electrodes on opposite sides of a body so that a first evoked electrode is positioned on a left side of the body and a second evoked electrode is positioned on a right side of the body at a position that corresponds to where the first evoked electrode is positioned on the left side of the body;
    positioning sensors on the opposite sides of the body via headgear to simultaneously position the sensors on the body to detect brain reaction to electrical current passed into the body for a pre-selected number of shocks,
    communicatively connecting the evoked electrodes and the sensors to a computer device having non-transitory memory connected to a processor;
    positioning a reference sensor on the body so that the reference sensor is located on a central region of a forehead at a location that is between a first sensor of the sensors that is positioned on a left side of a head of the body and a second sensor of the sensors that is positioned on a right side of the head of the body; and
    the computer device utilizing the reference sensor to determine that at least one of the sensors needs to be re-positioned so that the sensors on opposite sides of the body have a pre-selected orientation;
    the computer device determining that at least one of the sensors needs to be re-positioned so that the sensors on opposite sides of the body have the pre-selected orientation and outputting an orientation warning to indicate at least one of the sensors needs to be repositioned for sensor orientation for repositioning at least one of the sensors on the body;
    after the at least one of the sensors is repositioned for sensor orientation based on the orientation warning output by the computer device, shocking the body via the evoked electrodes for the pre-selected number of shocks within a pre-selected time period, the computer device transmitting the electrical current to the evoked electrodes for the shocking of the body via the evoked electrodes, wherein the shocking of the body via the evoked electrodes for the pre-selected number of shocks within the pre-selected time period comprises passing an electrical current into the body via an electricity transmitter of the computer device that is connected to the evoked electrodes;
    the sensors positioned on the opposite sides of the body detecting data from the body as the body responds to the pre-selected number of shocks;
    the computer device receiving the detected data from the sensors;
    the computer device generating at least one of wave forms and curves that identify morphological features for responses from the pre-selected number of shocks that the opposite sides of the body are measured to have based on the detected data received from the sensors;
    the computer device comparing the morphological features to determine a difference between a morphological feature for the left side of the body and a morphological feature for the right side of the body that is at or exceeds a pre-selected threshold that is defined to indicate the left side of the body has a different somatosensory evoked potential responding to the shocks as compared to the right side of the body responding to the shocks for indication of a neurological condition requiring treatment, the neurological condition requiring treatment being a stroke; and
    the computer device generating a notification to identify a detection of the neurological condition in response to a result of the comparing of the morphological features indicating that the difference between the morphological feature for the left side of the body and the morphological feature for the right side of the body is at or exceeds the pre-selected threshold so that the neurological condition is identifiable prior to transporting the body to a care facility.

2. The method of claim 1, wherein one of the wave forms and the curves are generated from the detected data the computer device receives from the sensors, the detected data being measurement data measuring an electrical response the body has to the pre-selected number of shocks.

3. The method of claim 2, comprising:
    the computer device receiving the measurement data from the sensors and storing the measurement data in the memory; and
    wherein the morphological features are amplitudes; and
    the responses from the pre-selected number of shocks that the opposite sides of the body are electrical responses a central nervous system of the body has to the pre-selected number of shocks.

4. The method of claim 1, comprising:
    filtering the detected data received from the sensors to remove noise from the detected data for generating the at least one of the wave forms and the curves.

5. The method of claim 1, wherein the notification includes indicia identifying a location of a hospital determined to be equipped for providing care for the neurological condition.

6. The method of claim 5, comprising:
    the computer device communicating data to an output device for identifying directions for routing an ambulatory vehicle to the hospital.

7. The method of claim 5, comprising:
    the computer device communicating data to a communication system of the hospital relating to the detection of the neurological condition.

8. The method of claim 5, comprising:
    the computer device searching at least one data store to identify the hospital based on the detected neurological condition.

9. The method of claim 1, wherein the evoked electrodes are on pads that are adhesively attached to the body for removable attachment to the body; and wherein the sensors are on at least one pad that is adhesively attached to the body, the method further comprising:
    removing coverings that cover adhesive portions of the pads.

10. The method of claim 1, wherein the first evoked electrode is positioned adjacent a left wrist of the body and the second evoked electrode is positioned adjacent a right wrist of the body and the sensors are positioned on a head of the body.

11. The method of claim 9, wherein the pads having the evoked electrodes also have at least one of the sensors and wherein each of the coverings has indicia identifying a location on which the pad of that covering is to be positioned on the body.

12. The method of claim 1, wherein the evoked electrodes are on gloves and wherein the attaching of the evoked electrodes on opposite sides of the body comprises:
    inserting hands of the body into the gloves.

13. The method of claim 12, wherein the attaching of the evoked electrodes on opposite sides of the body also comprises:
    verifying that the gloves are not twisted.

14. The method of 1, wherein the orientation warning is output via a display.

15. The method of claim 1, comprising:

positioning at least one accelerometer on the body, the accelerometer being communicatively connected to the computer device;

the computer device increasing the electrical current for the shocks in response to receiving measurement data from the accelerometer indicating that the body failed to move a distance that met or exceeded a movement threshold in response to a shock.

16. The method of claim 1, comprising:

positioning a skin color detector on the body, the skin color detector being communicatively connectable to the computer device;

the computer device determining at least one of: a racial type of the body and an age of the body in response to measurement data received from the skin color detector.

17. The method of claim 1, wherein the sensors and evoked electrodes are attached to pads that include indicia indicating how the pads are to be positioned on the body for positioning of the sensors and the evoked electrodes.

18. The method of claim 1, wherein the notification includes indicia identifying a location of a hospital determined to be equipped for providing care for the neurological condition, the method also comprising:

the computer device searching at least one data store to identify the hospital based on the detected neurological condition;

the computer device communicating data to a communication device of the hospital relating to the detection of the neurological condition;

the computer device communicating data to an output device for identifying directions for routing an ambulatory vehicle to the hospital; and transporting the body to the hospital after the notification is output via the computer device based on the directions for routing the ambulatory vehicle to the hospital; and wherein the computer device is connectable to a power source, the power source being an engine of the ambulatory vehicle or a battery of the ambulatory vehicle.

19. The method of claim 1, comprising:

the computer device determining that the evoked electrodes are incorrectly positioned relative to each other and generating an evoked electrode positioning warning to indicate the evoked electrodes are incorrectly positioned relative to each other to correct positioning of the evoked electrodes;

wherein the shocking of the body via the evoked electrodes for the pre-selected number of shocks within the pre-selected time period occurs after the evoked electrode positioning warning is generated.

* * * * *